United States Patent [19]

Györy et al.

[11] Patent Number: 4,588,713
[45] Date of Patent: May 13, 1986

[54] SELECTIVE BIOLOGICALLY ACTIVE 7-OXO-PROSTACYCLIN DERIVATIVES AND PHARMACEUTICAL COMPOSITIONS CONTAINING SAME

[75] Inventors: Peter Györy; Geza Galambos, both of Budapest; Károly Kánay, Ocsa; József Ivanics, Budapest; György Dorman, Budapest; Gábor Kovács, Budapest; István Stadler, Budapest; Sandor Virág, Budapest; István Tömösközi, Budapest; Peter Körmöczky, Budapest; Marianna Kovács, Budapest, all of Hungary

[73] Assignee: Chinoin Gyogyszer Vegyeszeti Termekek Gyara Rt., Budapest, Hungary

[21] Appl. No.: 691,340

[22] Filed: Jan. 14, 1985

[30] Foreign Application Priority Data

Jan. 13, 1984 [HU] Hungary ................ 128/84

[51] Int. Cl.⁴ .............. A61K 31/557; A61K 31/34; C07D 307/935
[52] U.S. Cl. ...................... 514/63; 514/460; 514/470; 549/214; 549/415; 549/465
[58] Field of Search ............ 549/214, 415, 465; 514/63, 460, 470

[56] References Cited

FOREIGN PATENT DOCUMENTS 3308561 9/1984 Fed. Rep. of Germany ...... 549/465

Primary Examiner—Henry R. Jiles
Assistant Examiner—Bernard I. Dentz
Attorney, Agent, or Firm—Karl F. Ross; Herbert Dubno

[57] ABSTRACT

Compounds of the formula

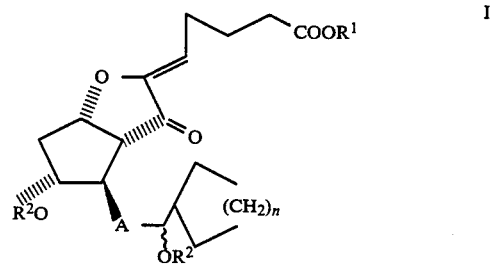

are disclosed wherein $R^1$ stands for hydrogen, $C_{1-4}$ straight or branched alkyl or pharmacologically acceptable cation, $R^2$ stands for hydrogen, $C_{1-4}$ alkanoyl, benzoyl, or benzoyl substituted by $C_{1-4}$ alkyl or halogen, and $R^2$ can further represent tetrahydropyranyl, trialkylsilyl or alkoxyalkyl, A stands for ethylene, cis or trans–vinylene or —C≡C—, n may represent 2, 3 or 4. The compounds are highly effective in the inhibition of thrombocyte aggregation while at the same time exert only a very small hypotensive effect.

9 Claims, No Drawings

SELECTIVE BIOLOGICALLY ACTIVE 7-OXO-PROSTACYCLIN DERIVATIVES AND PHARMACEUTICAL COMPOSITIONS CONTAINING SAME

The present invention relates to new biologically active compounds and to a process for the preparation thereof and to pharmaceutical compositions containing same.

The new compounds can be defined by the formula

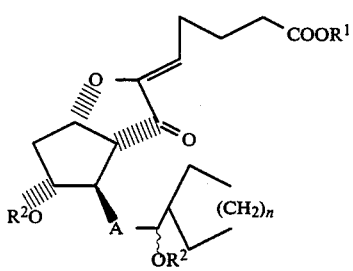

wherein
$R^1$ stands for hydrogen, $C_{1-4}$ straight or branched alkyl or a pharmacologically acceptable cation,
$R^2$ stand for hydrogen, $C_{1-4}$ alkanoyl, benzoyl, or benzoyl substituted by $C_{1-4}$ alkyl or halogen, and $R^2$ can further represent tetrahydropyranyl, trialkyl silyl or alkoxyalkyl,
A stands for ethylene, cis or trans-vinylene or —C≡C—,
n may represent 2, 3 or 4.

The compounds of the formula I may be in the form of racemates or optically active derivatives.

If $R^1$ stands for a pharmacologically acceptable cation, it may represent all organic or inorganic cations which do not show any detrimental (toxic) effect at the used dosage, such inorganic cations may be e.g. alkali metals, such as sodium, potassium, alkaline earth metals, such as calcium or magnesium ions. Unsubstituted ammonium ions or ammonium ions substituted by organic, preferably alkyl groups are also suitable. The substituted ammonium ions may bear further substituents such as hydroxyl or amino groups which favorably act upon the solubility and crystallization properties of the salts. One such preferred cation is the tris-(hydroxymethyl)-ammonium ion. $C_{1-4}$ straight and branched alkyl as referred to hereinafter can stand for methyl, ethyl, propyl or isopropyl, preferably methyl. $C_{1-4}$ alkanoyl in the definition of $R^2$ may stand for moieties derived from $C_{1-4}$ alkane carboxylic acid, such as formyl, propionyl, butyryl, and preferably acetyl. Substituted benzoyl may be substituted by one or more halogens, such as fluorine, chlorine, iodine, bromine or one or more $C_{1-4}$ straight or branched alkyl.

Trialkyl silyl groups are moieties consisting of three $C_{1-4}$ straight or branched same or different alkyl groups attached to the central silicon atom, such as trimethyl silyl, triethyl silyl, tripropyl silyl or dimethyl iso-propyl silyl, preferably dimethyl-tert. butyl silyl.

Alkoxyalkyl can be defined by the formula R—O—CH$_2$—wherein R is an alkyl group containing 1 to 4 carbon atoms, which may be straight or branched, preferably methyl.

The compounds of the formula I may be prepared by
(a) oxidizing a compound of the formula

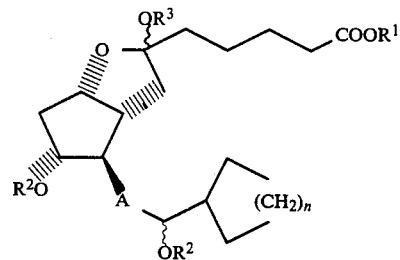

wherein $R^3$ stands for hydrogen or $C_{1-4}$ straight or branched alkyl, and $R^1, R^2, A$ and n are defined above, and heating the thus obtained compounds of the formula

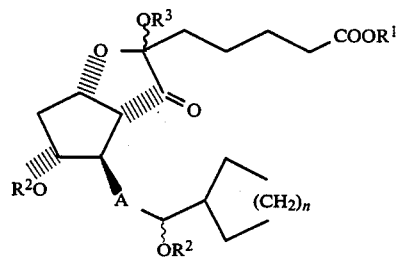

wherein $R^1$, $R^2$, $R^3$, A and n are given above, or
(b) oxidizing a compound of the formula

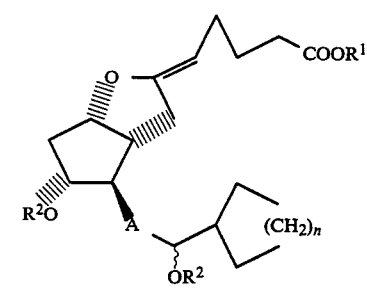

wherein $R^1$, $R^2$, A and n are as given above and optionally removing the protecting groups of the hydroxyl and/or carboxylic group and optionally forming salts.

The compounds of the formula I are stable and selective biologically active prostacycline derivatives.

Prostacyclin (PGI$_2$) the arachidonic acid metabolite which is wide spread in mammal organisms has been discovered in 1976. The substance shows various pharmaceutically valuable biological activities.

It inhibits the aggregation of blood platelets, it displays fibrinolytic activity, it dilates the respiratory tract and blood vessels and reduces gastric acid secretion. It shows so called cytoprotective activity in various organs, such as stomach, liver, heart, kidney, it eliminates the destructive consequences of various damaging effects occurring in said organs or it cures the organs.

There are two problems preventing the extensive use of PGI$_2$. One is the chemical and biological instability, i.e. the very short biological half-life, thus its route of administration can only be a special method of treatment, e.g. it can be administered by infusion. The other problem is the occurrence of several side-effects, which can sometimes be observed along with the desired effect due to the complex biological spectrum of activity.

The preparation of 7-oxo-PGI$_2$ derivatives which are more stable than the natural PGI$_2$ was first disclosed in U.S. Pat. No. 4,330,553. The chemical stability of the disclosed compounds is better—e.g. they can be stored in aqueous solution as well—and their spectrum of activity is substantially the same as that of PGI$_2$ (J. Med. Chem. 25, 105 (1982)).

The preparation of similar 7-oxo-PGI$_2$ derivatives is described in BE-PS No. 890 390. The common property of the 7-oxo-PGI$_2$ analogs mentioned above is that like the biological activity of PGI$_2$ their biological activity is not selective.

The new 7-oxo-PGI$_2$ derivatives according to the invention have the same spectrum of activity as PGI$_2$, but unexpectedly we have found that the new compound acts biologically more selectively than 7-oxo-PGI$_2$ derivatives known from the state of the art, while their stability is about the same. The selectivity is prostacyclin activity with reduced hypotensive effects. Accordingly the antiaggregation activity is higher.

The compounds of the formula I are prepared as given above. The details of the embodiments of the above methods are as follows:

(a) A compound of the formula IV is oxidized in a water-containing organic solvent, preferably dioxan or dimethoxy ethane by using 1.1 to 10 equivalents, preferably 1.3 to 1.5 equivalents of selenium dioxide at a temperature ranging from 20° to 200° C., preferably 50° to 100° C. The thus obtained compound of the formula II is then heated in the presence of an acid catalyst in organic solvents, preferably in benzene or toluene or halogenated solvents, such as chlorinated hydrocarbons, preferably in chloroform or dipolar aprotic solvents, such as dimethyl sulfoxide, preferably in dimethylformamide or without any solvent and thus a compound of the formula I is obtained. As acid catalyst p-toluene sulfonic acid or sulfuric are preferred. Compounds of the formula II can be heated at 50° to 200° C., preferably at 60° to 90° C., with or without water separation. The preferred way is to perform the heating in the presence of p-toluene sulfonic acid in benzene or toluene at 60° C. while a water trap is used.

The compounds of the formula IV are known from the literature or they can be prepared by analogous methods, see e.g. R. H. Johnson et al, J.A.C.S., Vol. 100, P. 7690 (1976). According to another preferred method of the invention a compound of the formula III may be oxidized to a compound of the formula I at a temperature ranging from 20° to 200° C. with 1.1 to 10 equivalents of selenium dioxide in an anhydrous organic solvent, such as an ether type solvent, preferably dioxan or dimethoxyethane. The reaction is preferably conducted in dioxan with 1.3 to 1.5 equivalents of selenium dioxide at 80° to 90° C.

The compounds of the formula III are known from the state of art or may be prepared by analogous methods (R. F. Newton et al: Synthesis 1984, 449.)

The hydroxyl groups at positions 11 and 15 of the starting materials of the formulae III and IV can be blocked by blocking various acyl groups, trialkyl silyl groups, alkoxy alkyl groups and tetrahydropyranyl as defined above. The introduction of the blocking groups may be carried out by methods known per se, and this may be important in order to achieve better yield. The above blocking groups may be removed—if desired— from the compounds of the formula I by methods known per se. The alkoxyalkyl groups or the tetrahydropyranyl groups may be removed by acid hydrolysis and the trialkyl silyl group may be removed by potassium fluoride or also in the presence of acid. The acyl group are hydrolized in a basic medium.

Those compounds of the formula I wherein $R^1$ stands for $C_{1-4}$ straight or branched alkyl may be converted to a salt containing a pharmacologically acceptable cation by methods known per se. In the course of the salt formation the ester group is split off under basic conditions. As a base alkaline or alkaline earth metal hydroxides, alkoxides are used in aqueous or anhydrous alcoholic solutions. As a base sodium methoxide and as a solvent anhydrous methanol is used. Carboxylic acids may be released from the aqueous solutions of the thus obtained salts by careful acidifying, and said carboxylic acids can be dissolved in organic solvents and converted to further salts e.g. trimethonium salt by reacting same acids with aliphatic and aromatic amines.

One characteristic representative of the compounds of the formula I is the sodium salt of 7-oxo-16,17,18,19,20-pentanor-15-cyclopentyl-PGI$_2$.

The selective biological activity of these compounds may be studied by investigating the antiaggregation and hypotensive activity simultaneously. Anti-aggregation activity was measured in vitro according to Born Nature, 214, 927 (1962) on human plasma enriched with thrombocytes in an aggregation induced by 2 $\mu$m ADP, whereas the haemodynamic activity was obtained from the blood pressure reducing activity of the compound administered in an i.v. bolus injection to an anaesthetized cat with an open-chest.

| | anti-aggregation IC$_{50}$ ng/ml | relative efficiency $H^1$ | hypotensive activity ED$_{50}$ $\mu$g/kg | relative efficiency $H^2$ | $H^1/H^2$ |
|---|---|---|---|---|---|
| PGI$_2$—Na | 1 | 1 | 0.16 | 1 | 1 |
| 7-oxo-PGI$_2$—Na | 15 | 0.086 | 6.5 | 0.024 | 2.75 |
| 16,17,18,19,20-pentanor-15-cyclopentyl-7-oxo-PGI$_2$—Na | 1.6 | 0.625 | 21.2 | 0.0075 | 83.1 |

It can be seen that the cyclopentyl analog is about hundred times more selective than prostacycline and it is considerably more selective than the sodium salt of 7-oxo-PGI$_2$ disclosed in U.S. Pat. No. 4,330,533.

A particular advantage of the compounds of the formula I is that they can be administered orally, too.

Due to their biological activity the compounds according to the invention may be used as active ingredients of pharmaceutical compositions. Said compositions can be used for the prevention and curing of diseases like peripheral diseases of vessels (atherosclerosis obliterans, Burger-disease, diabeticus angiopethia), for the improvement of the circulation of the limbs and for the reduction of the severeness of heart infarct and the amount of mortality.

The pharmaceutical compositions are suitable for the reduction of the intensity and number of attacks in several types of angina diseases and for treating other circulation diseases of various types such as pulmonary hypertension and heart insufficiency. They can show a valuable effect in prevention and treating cerebral ischaemias and can be used for treating asthma, diseases of the gastrointestinal system, such as ulcer, etc. and liver and pancreas diseases. The compositions are further suitable for the prevention of the loss of blood platelets alone or combined with heparin in the case of extra-corporal circulation (kidney chemodialysis, heart-lung machine). A further use is the inhibition of metastasis in patients suffering from tumors.

The pharmaceutical compositions according to the invention may be administered intravenously, subcutaneously, intramuscularly and orally (gastrointestinally) as well. The required amount is 0.0001 to 10 mg. per kg. of body weight. The exact dosage depends on the severity of the disease, on the rate of effectiveness of the medicine, on the susceptibility of the patient or the organ to be treated and on the response ability of the patient. The best way of administration and the necessary dosage can be determined by someone skilled in the art without any difficulty.

When preparing the pharmaceutical compositions the conventionally used filling agents, diluents, agents influencing the flavor and aroma, agents facilitating formation, adjusting pH and osmotic pressure, stabilizers, agents promoting resorption etc. and other excipients may be used. The prepared compositions may be solid (tablets, capsules, dragees, powders, pills), liquid (infusion, inhalant or injectable solutions, compress liquids, liquid medicines, drops etc.) or semi liquid/cremes, ointments, balsams, suppositories etc.

The disclosed active ingredients may be used alone or combined with other active ingredients.

EXAMPLES

EXAMPLE 1

Methyl ester of 6-hydroxy-7-oxo-11,15-diacetyl-16,17,18,19,20-pentanor-15-cyclopentyl-PGI$_1$ 605 mg. (1.25 mmole) of methyl ester of 6-methoxy-11,15-diacetyl-16,17,18,19,20-pentanor-15-cyclopentyl-PGI$_1$ are dissolved in a mixture of 6 ml. of dioxan and 0.5 ml. of water 210 mg. (1.89 mmole) of selenium dioxide are added and the reaction mixture is stirred for 2 hours. When the reaction is completed the mixture is filtered, the solvent is removed in vacuo. The residue is diluted with 50 ml. of ethyl acetate, washed with 2×10 ml. of water, a 5% sodium hydrogen carbonate solution until pH=7.5–8, then it is washed with a saturated salt solution and dried above magnesium sulphate. The thus obtained crude product is chromatographed on 200 g. of Reanal Kieselgel G adsorbent and eluted with a 50% mixture of hexane and ethyl acetate by short column chromatography. 380 g. of methyl ester of 6-hydroxy-7-oxo-11,15-diacetyl-16,17,18,19,20-pentanor-15-cyclopentyl-PGI$_1$ are isolated in the form of a red oil. Thin layer chromatography: $R_f$ 0.18 (1 hexane—1 ethyl acetate).

IR (cm$^{-1}$, film): 3400, 2950, 1740, 1150.

EXAMPLE 2

Methyl ester of 7-oxo-11,15-diacetyl-16,17,18,19,20-pentanor-15-cyclopentyl-PGI$_2$ 380 mg. (0.79 mmole) of methyl ester of 6-hydroxy-7-oxo-11,15-diacetyl-16,17,18,19,20-pentanor-15-cyclopentyl-PGI$_1$ are dissolved in 30 ml. of benzene and to the solution 3 mg. of p-toluene-sulfonic are added and the mixture is stirred at room temperature for 15 minutes and at 60° C. for 3 hours. In the course of the heating a total of 5 ml. of benzene are distilled to the water trap. When the reaction is completed the reaction mixture is cooled to room temperature and stirred for 2 hours with 0.6 g. of neutral aluminum oxide. The aluminum oxide is filtered, the filtrate is partially evaporated and the substance is chromatographed on 20 g. Kieselgel G. adsorbent by short column chromatography and as eluant a 2:1 mixture of hexane and ethyl diacetyl-16,17,18,19,20-pentanor-15-cyclopentyl-PGI$_2$ are obtained in the form of a colorless oil.

$R_f$=0.43 (1 hexane—1 ethyl acetate).
IR (cm$^{-1}$, film): 2950, 1745, 1715, 1650, 1160.
UV $\lambda_{max}$ (nm)=287 log$\xi$=3.96.

EXAMPLE 3

Methyl ester of 7-oxo-16,17,18,19,20-pentanor-15-cyclopentyl-PGI$_2$ 198 mg. (0.43 mmole) of methyl ester of 7-oxo-11,15 diacetyl-16,17,18,19,20-pentanor-15-cyclopentyl-PGI$_2$ are dissolved in 30 ml. of anhydrous methanol and to the solution 0.25 ml. of a 1 M methanolic sodium methoxide solution is added. The reaction mixture is stirred overnight at room temperature. Methanol is removed in vacuo at 0° C. and the substance is dissolved in a mixture of 50 ml. of ether and 7 ml. of water at 0° C. and after the separation of the layers the ether solution is washed with 10 ml. of saturated salt solution and stirred with 0.5 g. of neutral aluminum oxide and 0.2 g. of activated charcoal, filtered and finally dried above sodium sulphate in the presence of triethyl amine. After evaporation 135 mg. of methyl ester of pure 7-oxo-16,17,18, 19,20-pentanor-15-cyclopentyl-PGI$_2$ are obtained in the form of a colorless oil.

$R_f$=0.36 (1 hexane—1 acetate).
UV: $\lambda_{max}$=287 nm, log$\xi$=3.856.

EXAMPLE 4

Sodium salt of 7-oxo-16,17,18,19,20-pentanor-15-cyclopentyl-PGI$_2$ 220 mg. (0.63 mmole) of the methyl ester of 7-oxo-16,17,18,19,20-pentanor-15-cyclopentyl-PGI$_2$ are dissolved in 10 ml. of methanol, 2 ml. of 1 M aqueous sodium hydroxide solution are added and the mixture is stirred at 40° C. for 3 hours. Methanol is then removed in vacuo and the residue is dissolved in 20 ml. of distilled water. The aqueous solution is shaken out with 2×5 ml. of ether and the aqueous layer is acidified to pH=6 at 0° C. by adding 1 N sodium hydrogen sulphate solution and extracted with 2×10 ml. ethyl acetate. The aqueous layer is further acidified with sodium hydrogen sulphate solution to pH=4 at 0° C. and it is extracted again with 2×20 ml. ethyl acetate. All ethyl acetate organic layers are combined and washed with a 2×5 ml. saturated salt solution. The solution is stirred with 0.6 g. of neutral aluminum oxide and 0.2 g. of activated charcoal for 10 minutes and filtered. 20 ml. of water are added to the solution and pH is adjusted to 7.2–7.3 with 0.1 N sodium hydroxide solution. The two layers are separated, and the organic layer is shaken out with 10 ml. of water. The combined aqueous layer is evaporated and dried and thus 190 mg. of sodium salt of 7-oxo-16,17,18,19,20-pentanor-15-cyclopentyl-PGI$_2$ are obtained. In order to use the aqueous solution of the title compound the aqueous solution need not be evaporated, the solution can be directly used.

Tlc.: the substance is developed in the form of acid.
$R_f$=0.30 (20 benzene —10 dioxan —1 acetic acid).
IR: (cm$^{-1}$, KBr): 3500–3200, 2940, 2850, 1720, 1650, 1615.

EXAMPLE 5

Sodium salt of 7-oxo-16,17,18,19,20-pentanor-15-cyclopentyl-PGI$_2$ 340 mg. (0.74 mmole) of the methyl ester of 7-oxo-16,17,18,19,20-pentanor-15-cyclopentyl-PGI$_2$ are dissolved in 50 ml. of methanol and to the solution 0.5 ml. of 1 M methanolic sodium methoxide solution is added and the reaction mixture is stirred for 10 hours at room temperature. After removing part of the methanol (total volume about 20 ml) 5 ml. of an 1 N sodium hydroxide solution is added and the solution is stirred for 3 hours at 40° C. Methanol is distilled off in vacuo. The reaction mixture is worked up as described in the previous Example.

EXAMPLE 6

Methyl ester of 7-oxo-11,15-diacetyl-16,17,18,19,20-pentanor-15-cyclohexyl-PGI$_2$ To a solution of 1010 mg. (2.25 mmole) of 11,15-diacetyl-16,17,18,19,20-pentanor-15-cyclohexyl-PGI$_2$ in 20 ml. of anhydrous dioxan 374 mg. (3.4 mmole) of selenium dioxide are added. The reaction mixture is stirred for 2.5 hours at 85° C. under an argon atmosphere. When the reaction is completed to the reaction mixture 1 g. of neutral aluminum oxide is added at room temperature and it is stirred for 15 minutes. After the filtration of the mixture it is partially evaporated and purified by short column chromatography. As adsorbent 200 g. of Kieselgel G and as eluant a 1:1 mixture of hexane and ethyl acetate is used. 200 g. of the title product are isolated in the form of colorless oil.

R$_f$=0.40 (hexane and ethyl acetate 1:1).
IR: (cm$^{-1}$, film) =2950, 2860, 1740, 1715, 1650.

EXAMPLE 7

Methyl ester of 7-oxo-16,17,18,19,20-pentanor-15-cyclohexyl-PGI$_2$

To a solution of 220 mg. (0.46 mmole) of methyl ester of 7-oxo-11,15-diacetyl-16,17,18,19,20-pentanor-15-cyclohexyl-PGI$_2$ in 30 ml. of anhydrous methanol 0.25 ml. of a 1 M methanolic sodium methoxide solution is added. The reaction mixture is stirred overnight at room temperature under an argon atmosphere. Methanol is then removed in vacuo, the substance is dissolved at 0° with a mixture of 50 ml of ether and 7 ml. of water, the ether solution is washed with 10 ml. of a saturated salt solution after the separation of the layers and stirred with 0.5 g. of neutral aluminum oxide and 0.2 g. of active charcoal for 10 minutes and finally dried above sodium sulphate. After evaporation 148 mg. of the title compound are obtained in the form of a colorless oil.

R$_f$: 0.34 (1 hexane—1 acetone).
UV: $\lambda_{max}$=289 nm, log$\epsilon$=3.903.

EXAMPLE 8

Tris-(hydroxymethyl)-amino-methane salt of 7-oxo-16,17,18,19,20-pentanor-15-cyclopentyl-PGI$_2$ 540 mg. (1.35 mmole) sodium salt of 7-oxo-16,17,18,19,20-pentanor-15-cyclopentyl-PGI$_2$ are dissolved in 10 ml. of water and the solution is acidified with 1 N sodium hydrogen sulphate solution to pH =4 and extracted with 2×20 ml. ethyl acetate. The combined organic layers are shaken out with saturated salt solution and dried above sodium sulphate. Sodium sulphate is filtered off and then 175 mg. (1.45 mmole) of tris-(hydroxymethyl)-amino-methane are added to the solution and it is stirred for 2 hours at 40° C. and allowed to stand for 12 hours. The reaction mixture is then evaporated to dryness and thus 510 mg. of title compound are isolated.

Thin layer chromatography: identical with the previous compounds in acid form.

UC /EtOH: $\lambda_{max}$=288 nm, lg$\epsilon$=3.965.

EXAMPLE 9

Methyl ester of 6-hydroxy-7-oxo-11,15-diacetyl-13,14-didehydro-16,17,18,19,20-pentanor-15-cyclohexyl-PGI$_2$ 1850 mg. (3.76 mmole) of 6-methoxy-11,15-diacetyl-13,14-didehydro-16,17,18,19,20-pentanor-15-cyclohexyl-PGI$_1$-methyl ester are dissolved in 15 ml. dioxan and 2 ml. water and to the solution 650 mg. (5.86 mmole) of selenium dioxide are added and the reaction mixture is stirred for 2 hours at 60° C. The reaction mixture is then filtered, dioxan is removed at reduced pressure and the residue is diluted with 200 ml. of ethyl acetate. The solution is washed subsequently with 2×50 ml. of water, 5% sodium hydrogen carbonate solution until pH=7.5-8, saturated salt solution, and it is dried above magnesium sulphate. The product is isolated by short column chromatography—by using 500 g. Kieselgel G silicagel, and as eluant an 1:1 mixture of hexane and ethyl acetate in an amount of 790 mg. in the form of a red oil.

Thin layer chromatography: R$_f$=0.20 (hexane-ethyl acetate).

IR (cm$^{-1}$, film): 3400, 2950, 2230, 1740, 1160.

EXAMPLE 10

Methyl ester of 7-oxo-11,15-diacetyl-13,14-didehydro-16,17,18,19,20-pentanor-15-cyclohexyl-PGI$_2$ 750 mg. (1.52 mmole) of 6-hydroxy-7-oxo-11,15-diacetyl-13,14-didehydro-16,17,18,19,20-pentanor-15-cyclohexyl-PGI$_1$-methyl ester are dissolved in 30 ml. of benzene and to the solution 5 mg. of p-toluene sulfonic acid are added whereafter the mixture is stirred for 15 minutes at room temperature and for 3 hours at 60°-65° C. while the solvent-water is distilled off. During the reaction about 10 ml. of benzene are distilled off. The reaction mixture is then cooled to room temperature and stirred for 3 hours with 1 g. of neutral aluminum oxide. Aluminum oxide is removed by filtration and the reaction mixture is purified by short column chromatography (100 g. of Kieselgel G silicagel, eluant: 2 hexane—1 ethyl acetate). Thus 286 mg. of title product are isolated in the form of colorless oil.

Thin layer chromatography: R$_f$=0.56 (1 hexane 1 ethyl acetate).

UV (EtOH): $\lambda_{max}$=285 nm log$\xi$=4.01.

EXAMPLE 11

Methyl ester of 7-oxo-13,14-didehydro-16,17,18,19,20-pentanor-15-cyclohexyl-PGI$_2$ 250 mg. (0.53 mmole) of methyl ester of 7-oxo-13,14-didehydro-11,15-diacetyl-16,17,18,19,20-pentanor-15-cyclohexyl-PGI$_2$ are dissolved in 50 ml. of anhydrous methanol and to the solution 1 ml. (1 mmole) of 1 M methanolic sodium methoxide solution is added. The reaction mixture is allowed to stand overnight and the solvent is removed at reduced pressure at 0° C. The residue is dissolved in the mixture of 50 ml. of ether and 5 ml. of water, the separated organic layer is washed with 10 ml. of saturated salt solution, stirred with 0.5 g. of neutral aluminum oxide and 0.5 g. activated charcoal for 10 minutes, filtered and dried above sodium sulphate in the presence of triethyl amine. After evaporation 143 mg. of the title compound are obtained in the form of a colorless oil.

Thin layer chromatography: $R_f=0.21$ (1 hexane—1 ethyl acetate).

UV (EtoH): $\lambda_{max}=287$ nm $\log\xi=3.98$.

EXAMPLE 12

Sodium salt of 7-oxo-13,14-didehydro-16,17,18,19,20-pentanor-15-cyclohexyl-PGI$_2$ 113 mg. (0.31 mmole) of methyl ester of 7-oxo-13,14-didehydro-16,17,18,19,20-pentanor-15-cyclohexyl-PGI$_2$ are dissolved in 7 ml of methanol and 3 ml. of water and to the solution 2 ml. (2 mmole) 1 M aqueous sodium hydroxide solution is added and the solution is stirred for 3 hours at room temperature. Methanol is then removed at reduced pressure and to the residue 10 ml. of distilled water are added. The aqueous solution is washed with 2×5 ml. of ether and cooled to 0° C. and acidified to pH=5-6 by adding about 2 ml. of cold 1 M aqueous sodium hydrogen sulphate solution and finally extracted with 2×10 ml. of ethyl acetate. The aqueous layer is further acidified with 0.1 M sodium hydrogen sulphate solution to pH=3-4 washed with 2×20 ml. of ethyl acetate. The combined ethyl acetate layers are washed with 2×10 ml. of saturated salt solution, stirred for 10 minutes on 0.5 g. of neutral aluminum oxide and 0.2 g. of activated charcoal and filtered. To the filtrate 20 ml. of water are added and the pH is adjusted to 7.4-7.6 by adding 0.1 N sodium hydroxide solution. The organic layer is shaken out with 10 ml. of water and the combined aqueous layers are evaporated and thus 78 mg. of title compound are obtained.

Thin layer chromatography: the substance is developed in the form of acid $R_f=0.30$ (20 benzene—10 dioxan—1 acetic acid).

IR (KBr, cm$^{-1}$): 3300, 2950, 2220, 1720, 1645.

We claim:

1. A compound of the formula (I)

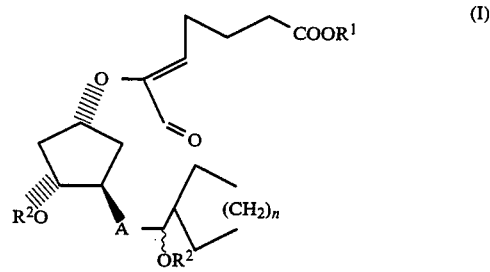

wherein
$R^1$ stands for hydrogen, $C_{1-4}$ straight or branched alkyl or a pharmacologically acceptable cation,
$R^2$ stands for hydrogen, $C_{1-4}$ alkanoyl, benzoyl, or benzoyl substituted by $C_{1-4}$ alkyl or halogen, and $R^2$ can further represent tetrahydropyranyl, trialkylsilyl or alkoxyalkyl,
A stands for ethylene, cis or trans-vinylene or —C≡C—, and
n may represent 2, 3 or 4.

2. 7-oxo-11,15-diacethyl-16,17,18,19,20-pentanor-15-cyclopentyl-PGI$_2$ methyl ester as defined in claim 1.

3. Methyl ester of 7-oxo-16,17,18,19,20-pentanor-15-cyclopentyl-PGI$_2$ as defined in claim 1.

4. Sodium salt of 7-oxo-16,17,18,19,20-pentanor-15-cyclopentyl-PGI$_2$ as defined in claim 1.

5. Methyl ester of 7-oxo-16,17,18,19,20-pentanor-15-cyclohexyl-PGI$_2$ as defined in claim 1.

6. Methyl ester of 7-oxo-11,15-diacetyl-16,17,18,19,20-pentanor-15-cyclohexyl as defined in claim 1.

7. Tris-(hydroxymethyl)-amino-methane salt of 7-oxo-16,17,18,19,20-pentanor-15-cyclopentyl-PGI$_2$ as defined in claim 1.

8. An anticoagulant and trachea relaxing pharmaceutical composition comprising as active ingredient a pharmaceutically effective amount of compound of the formula I as defined in claim 1, along with a pharmaceutically acceptable inert carrier or diluent.

9. A method of inhibiting thrombocyte aggregation in an animal subject which comprises the step of administering to said animal subject a pharmaceutically effective amount of the compound of the formula (I) as defined in claim 1.

* * * * *